US008722397B2

(12) United States Patent
Hino et al.

(10) Patent No.: US 8,722,397 B2
(45) Date of Patent: May 13, 2014

(54) METHOD FOR DETECTING AND QUANTIFYING ENDOGENOUS WHEAT DNA SEQUENCE

(75) Inventors: Akihiro Hino, Tsukuba (JP); Takashi Kodama, Tsukuba (JP); Mayu Iida, Ohbu (JP); Hirohito Yamakawa, Fujimino (JP); Satomi Nozaki, Fujimino (JP); Katsuyuki Hayakawa, Fujimino (JP)

(73) Assignees: Nisshin Seifun Group Inc., Tokyo (JP); Incorporated Administrative Agency National Agriculture and Food Research Organization, Tsukuba-shi (JP)

( * ) Notice: Subject to any disclaimer, the term of this patent is extended or adjusted under 35 U.S.C. 154(b) by 172 days.

(21) Appl. No.: 13/218,385

(22) Filed: Aug. 25, 2011

(65) Prior Publication Data
US 2012/0009585 A1    Jan. 12, 2012

Related U.S. Application Data

(62) Division of application No. 11/578,107, filed as application No. PCT/JP2005/006784 on Apr. 6, 2005, now Pat. No. 8,030,463.

(30) Foreign Application Priority Data

Apr. 9, 2004 (JP) ................................ 2004-115687

(51) Int. Cl.
C12N 1/00 (2006.01)
C12Q 1/68 (2006.01)
C12P 19/34 (2006.01)

(52) U.S. Cl.
USPC ........ 435/320.1; 435/6.1; 435/6.11; 435/6.12

(58) Field of Classification Search
None
See application file for complete search history.

(56) References Cited

U.S. PATENT DOCUMENTS

| | | | |
|---|---|---|---|
| 8,030,463 B2 | 10/2011 | Hino et al. | |
| 8,173,400 B2 | 5/2012 | Imai et al. | |
| 2009/0011411 A1 | 1/2009 | Hino et al. | |
| 2010/0062432 A1 | 3/2010 | Imai et al. | |
| 2012/0009584 A1 | 1/2012 | Hino et al. | |
| 2012/0009586 A1 | 1/2012 | Hino et al. | |
| 2012/0040862 A1 | 2/2012 | Hino et al. | |
| 2012/0208992 A1 | 8/2012 | Imai et al. | |
| 2012/0214161 A1 | 8/2012 | Imai et al. | |
| 2012/0246748 A1 | 9/2012 | Guo et al. | |
| 2012/0258464 A1 | 10/2012 | Kitta et al. | |

FOREIGN PATENT DOCUMENTS

| | | |
|---|---|---|
| EP | 1 482 058 A1 | 12/2004 |
| EP | 1 736 543 | 12/2006 |
| EP | 2 019 136 A1 | 1/2009 |
| JP | 6-125669 | 5/1994 |
| JP | 7-501682 | 2/1995 |
| JP | 2003-284598 | 10/2003 |
| JP | 2009-082125 A | 4/2009 |
| WO | WO 91/13991 | 9/1991 |
| WO | WO 98/04737 | 2/1998 |
| WO | WO 03/068989 | 8/2003 |
| WO | WO 03/068989 A1 | 8/2003 |
| WO | WO 2005/097989 | 10/2005 |
| WO | WO 2007/132760 A1 | 11/2007 |

OTHER PUBLICATIONS

Yan et al., "Sequences of the *Waxy* Loci of Wheat: Utility in Analysis of Waxy Proteins and Developing Molecular Markers," *Biochemical Genetics*, 38(11/12): 391-411 (2000).
Comments on Statement of Reasons for Allowance filed Oct. 12, 2011, in U.S. Appl. No. 12/300,973.
Request for Continued Examination filed Dec. 7, 2011, in U.S. Appl. No. 12/300,973.
Notice of Allowance and Fee(s) Due mailed Jan. 6, 2012, in U.S. Appl. No. 12/300,973.
Office Action (Restriction Requirement) mailed Jan. 30, 2012, in U.S. Appl. No. 13/218,358.
GenBank Accession No. BT008973 (retrieved on-line), Jun. 2003, retrieved from http://www.ncbi.nlm.nih.gov/nuccore/BT008973.
U.S. Appl. No. 12/300,973: Notice of Allowance mailed Sep. 16, 2011.
U.S. Appl. No. 13/218,321: Office Action (Restriction Requirement) mailed Mar. 7, 2012.
U.S. Appl. No. 13/218,321: Response to Restriction Requirement filed Apr. 5, 2012.
U.S. Appl. No. 13/218,321: Office Action mailed May 3, 2012.
U.S. Appl. No. 13/218,358: Response to Restriction Requirement filed Feb. 28, 2012.
U.S. Appl. No. 13/218,358: Office Action mailed May 2, 2012.
U.S. Appl. No. 13/218,398: Office Action (Restriction Requirement) mailed Feb. 9, 2012.
U.S. Appl. No. 13/218,398: Response to Restriction Requirement filed Mar. 8, 2012.
U.S. Appl. No. 13/218,398: Office Action mailed Mar. 26, 2012.
"JAS Analytical Handbook, Manual of Assessment and Analysis for Genetically Modified Foods"; Revised Second Edition, 67 pages, (Jun. 20, 2002).
"Concerning Testing Methods for Foods Modified by Recombinant DNA Technology"; (Partially Revised), Notice No. 0618001 of the Food Sanitation Department, Ministry of Health, Labor and Welfare, pp. 1-18, (Jun. 18, 2003).

(Continued)

*Primary Examiner* — Young J Kim
(74) *Attorney, Agent, or Firm* — Finnegan, Henderson, Farabow, Garrett & Dunner LLP.

(57) ABSTRACT

A circular DNA is provided comprising endogenous DNA common to both genetically modified wheat and non-genetically modified wheat along with one or more pieces of DNA each having a sequence present specifically in a strain of genetically modified wheat. Also provided is a method for determining a mix rate of genetically modified wheat in a test sample.

4 Claims, 8 Drawing Sheets

(56) References Cited

OTHER PUBLICATIONS

"Concerning Testing Methods for Food Modified by Recombinant DNA Technology"; (Partially Revised), Notice No. 1113001 of the Food Sanitation Department, Ministry of Health, Labor and Welfare, p. 1, (Nov. 13, 2003).
Aoki et al.; "Three Sucrose Transporter Genes are Expressed in the Developing Grain of Hexaploid Wheat"; Plant Molecular Biology, vol. 50, pp. 453-462, (2002).
Waiblinger et al.; "A Screening Method for the Identification of "Genetically Modified" Food of Plant Origin" ; Foods Produced by Means of Genetic Engineering, $2^{nd}$ Status Report: BgVV, BgVV-Heft, pp. 118-122, (1997).
Köppel et al.; "Sensitive Method for the Detection of Genetically Engineered Soy Beans <<Roundup Ready™ >>"; Mitt. Gebiete Levensm, Hyg., vol. 88, pp. 164-175, (1997).
Murai et al.; "Isolation and Characterization of the Three *Waxy* Genes Encoding the Granule-Bound Starch Synthase in Hexaploid Wheat"; Gene, vol. 234, pp. 71-79, (1999).
International Search Report and Written Opinion for International Application No. PCT/JP2007/059727, (Jan. 15, 2009).
"Manual of Assessment and Analysis for Genetically Modified Foods," Revised Second Edition; JAS Analytical Test Handbook, Jun. 18, 2003.
"Concerning Test Methods for Foods Modified by Recombinant DNA Technology (Partially Revised)", Notice. No. 0618001 of the Food Sanitation Department, Ministry of Health, Labor and Welfare, Jun. 18, 2003.
"Concerning Test Methods for Foods Modified by Recombinant DNA Technology (Partially Revised)," Notice No. 1113001 of the Food Sanitation Department, Ministry of Health, Labor and Welfare, Nov. 13, 2003.
Aoki, Naohiro, et al.; "Three Sucrose Transporter Genes are Expressed in the Developing Grain of Hexaploid Wheat;" Plant Molecular Biology 50: 2002, pp. 453-462.
Waiblinger, H.U., et al. "A Screening Method for the Identification of Genetically Modified Food of Plant Origin;" Foods Produced by Means of Genetic Engineering, $2^{nd}$ Status Report, Jan. 1997; pp. 118-122.
Koppel, E., et al.; "Sensitive Method for the Detection of the Genetically Engineered Soy Bean 'Roundup Ready'"; Mitt. Gebiete Lebensm, Hyg. 88; 1997; pp. 164-175.
Murai, J. et al.; "Isolation and Characterization of the Three Waxy Genes Encoding the Granule-Bound Starch Synthase in Hexaploid Wheat," Gene, 234; Japan, May 3, 1999; pp. 71-79.
Ainsworth, Charles, et al.; "Expression, Organisation and Structure of the Genes Encoding the Waxy Protein (Granule-Bound Starch Synthase) in Wheat;" Plant Molecular Biology 22; 1993; pp. 67-82.
Raines, C.A., et al., "A Novel Proline-Rich Protein From Wheat," Plant Molecular Biology 16; 1991; and Abstract, retrieved on Jun. 1, 2007 from www.ncbi.nlm.nih.gov/pubmed/1714320?dopt=AbstractPlus; Apr. 1991, pp. 663-670.
Raines, C.A. et al.; "*T. aestivum* mRNA for a proline-rich protein;" retrieved on Sep. 12, 1993 from www.ncbi.nlm.nih.gov/entrez/viewer.fcgi?db=nucleotideval=21841.
European Search Report dated Apr. 17, 2009 for Application No. 05728798.9-2403.
Allmann, Michael, et al., Polymerase chain reaction (PCR): a possible alternative to immunochemical methods assuring safety and quality of food, Z Lebensm Unters Forsch (1993) 196;248-251.
Hübner, Philipp, et al., Validation of PCR Methods for Quantitation of Genetically Modified Plants in Food, Journal of AOAC International (2001) 84(6):1855-1864.
Iida, Mayu, et al., Development of Taxon-Specific Sequences of Common Wheat for the Detection of Genetically Modified Wheat, Journal of Agricultural and Food Chemistry (2005) 53:6294-6300.
Studer, Edgar, et al., Quantitative Competitive PCR for the Detection of Genetically Modified Soybean and Maize, Z Lebensm Unters Forsch A (1998) 207:207-213.
Terzi, Valeria, et al., Development of Analytical Systems based on Real-Time PCR for *Triticum* Species-Specific Detection and Quantitation of Bread Wheat Contamination in Semolina and Pasta, Journal of Cereal Science (2003) 38:87-94.
Yamakawa, Hirohito, et al., Specific Detection of Wheat Residues in Processed Foods by Polymerase Chain Reaction, Bioscience, Biotechnology, and Biochemistry (2007) 71(10): 2561-2564.
Feuillet et al., "Genetic and Physical Characterization of the *LR1* Leaf Rust Resistance Locus in Wheat (*Triticum aestivum* L.)," *Molecular and General Genetics*, 248(5): 553-562 (1995).
Ling et al., "High-Resolution Mapping of the Leaf Rust Disease Resistance Gene Lr1 in Wheat and Characterization of BAC Clones From the Lr1 Locus," *Theoretical and Applied Genetics*, 106(5): 875-882 (2003).
McNeil et al., "Amplification of DNA sequences in wheat and its relatives: the Dgas44 and R350 families of repetitive sequences," *Genome*, 37(2):320-327 (1994).
Nakamura et al., "Rapid classification of partial waxy wheats using PCR-based markers," Genome 45(6): 1150-1156 (2002).
European Search Report in corresponding EP Application No. 09015931.0, dated Apr. 14, 2010.
European Search Report in corresponding EP Application No. 09015932.8, dated Apr. 12, 2010.
European Search Report in corresponding EP Application No. EP 07743162.5, dated Jun. 10, 2010.
Database record for GenBank Accession No. AF113844, *Triticum aestivum granule-bound starch synthase precursor (Wx-D1) mRNA, Wx-D1b allele*, complete cds (Apr. 20, 1999).
Database record for GenBank Accession No. AF408845, *Triticum aestivum sucrose transporter SUT1D gene*, complete cds (Mar. 19, 2002).
Database record for GenBank Accession No. AJ440705, *Triticum aestivum GSS clone PSR1205 forward sequence, genomic survey sequence* (Jul. 31, 2003).
Database record for GenBank Accession No. J02817, *Wheat gibberellin responsive protein gene*, complete cds (Apr. 27, 1993).
Database record for GenBank Accession No. S79982, *Lr1 (TLR621)=leaf rust resistance gene [Triticum aestivum=wheat, Genomic, 915 nt]* (Feb. 12, 1997).
Database record for GenBank Accession No. S79983, *Lr1 (TH621)=leaf rust resistance gene[Triticum aestivum=wheat, Genomic, 892 nt]* (Feb. 12, 1997).
Lowe et al., "A computer program for selection of oligonucleotide primers for polymerase chain reactions," *Nucleic Acids Research*, 18(7): 1757-1761 (1990).
Office Action mailed Mar. 29, 2011, in U.S. Appl. No. 12/300,973.
Reply to Office Action filed Jun. 29, 2011, in U.S. Appl. No. 12/300,973.
Notice of Allowance mailed May 31, 2011, in U.S. Appl. No. 12/300,973.
U.S. Appl. No. 13/710,910, filed Dec. 11, 2012, by Nino et al.: Non-final Office Action, dated Jul. 5, 2013.
U.S. Appl. No. 13/366,062, filed Feb. 3, 2012, by Imai et al.: Advisory Action, dated Jun. 12, 2013.
Advisory Action issued in U.S. Appl. No. 13/366,190 mailed on Aug. 12, 2013.
Ron Ning et al., "Novel Reference Gene, PKABA1, Used in a Duplex Real-Time Polymerase Chain Reaction for Detection and Quantitation of Wheat- and Barley- Derived DNA" *Journal of Agricultural and Food Chemistry*, 54:682-687 (2006).
Ahern, "Biochemical, Reagent Kits Offer Scientists Good Return on Investment" *The Scientist*, 20:20,22 (Jul. 24, 1995).
International Preliminary Report on Patentability for International Application No. PCT/JP2010/072809, issued Jul. 10, 2012.
International Search Report and Written Opinion from the Japanese Patent Office for International Application No. PCT/JP2010/072809, mailed Jan. 25, 2011.
International Search Report and Written Opinion issued in International Patent Application No. PCT/JP2005/006784, dated Jul. 19, 2005, English translations.

(56) References Cited

OTHER PUBLICATIONS

Yang et al., "Genomics, Molecular Genetic & Biotechnology. A Rapid and Direct Approach to Identify Promoters That Confer High Levels of Gene Expression in Monocots" *Crop Science*, 43:1805-1813 (2003).

U.S. Appl. No. 13/366,062, filed Feb. 3, 2012, by !mai et al.: Non-Final Office Action, mailed Sep. 23, 2013.

U.S. Appl. No. 13/710,910, filed Dec. 11, 2012, by Akihiro Hino et al.: Final Office Action mailed Jan. 29, 2014.

US 8,722,397 B2

METHOD FOR DETECTING AND QUANTIFYING ENDOGENOUS WHEAT DNA SEQUENCE

This is a divisional of U.S. patent application Ser. No. 11/578,107, filed Aug. 12, 2008, now U.S. Pat. No. 8,030,463 which is the National Stage of PCT International Application No. PCT/JP2005/006784, filed Apr. 6, 2005, and Japanese Application No. JP 2004-115687, filed on Apr. 9, 2004, all of which are incorporated herein by reference.

BACKGROUND

The present invention relates to a method for detecting or quantifying an endogenous DNA sequence of wheat in a test sample, and relates in particular to an endogenous wheat DNA detection or quantification method to be used when determining the contamination rate of genetically modified wheat contained in food materials or processed foods.

In Japan, 50 or more varieties of genetically modified crops (hereunder "GMOs") including corn, soy beans and potatoes have passed safety assessment and been approved for import and sale. At the same time, foods containing GMOs must be labeled as such in accordance with the "Labeling Standard for Genetically Modified Foods established by the Ministry of Agriculture, Forestry and Fisheries based on Article 7, paragraph 1 of the Quality Labeling Standard for Processed Foods and Article 7, paragraph 1 of the Quality Labeling Standard for Fresh Food" (Notification No. 517 of the Ministry of Agriculture, Forestry and Fisheries, Mar. 31, 2000) and the "Enforcement of Ministerial Ordinance amending in part the Ministerial Ordinance on Food Sanitation Law Enforcement Regulations and Compositional Standards, etc. for Milk and Milk Products" (Notice No. 79 of the Food Sanitation Department, Ministry of Health, Labor and Welfare, Mar. 15, 2001).

In other countries, however, GMOs may in some cases be cultivated together with non-GMOs once the safety evaluation has been completed, or contamination may occur during the process of distribution after harvest. Moreover, the makers of food products and the like often contract the manufacture of processed foods out to manufacturing companies, and even if they stipulate that non-GMOs should be used, if GMOs are used in the plants of the manufacturing companies, the processed foods may become contaminated by small quantities of GMOs. Consequently, in order to fulfill their labeling obligations makers of food products and the like must assess and analyze the final processed food products to verify that they are not contaminated with GMOs.

Methods of detecting GMOs in test samples of processed foods and their raw materials, etc. include methods of detecting modified DNA by polymerase chain reaction (PCR) and methods of detecting modified proteins by ELISA, but in the case of processed foods GMOs must be detected by PCR because the proteins have often been denatured by heat or pressure and cannot be detected accurately by ELISA.

Methods of assessment and analysis include the methods described in the JAS Analytical Handbook, Manual of Assessment and Analysis for Genetically Modified Foods, Revised Second Edition and those described in "Concerning Testing Methods for Foods Modified by Recombinant DNA Technology (Partially Revised)" (Notice No. 0618002 of the Food Sanitation Department, Ministry of Health, Labor and Welfare, Jun. 18, 2003). These describe that in the testing and analysis of GMOs, it is necessary to perform PCR using a primer pair recognizing the endogenous DNA of each agricultural product and to verify that a PCR product of the expected length is obtained, in order to verify that DNA extracted from the test sample can be amplified by PCR. When quantifying a GMO contained in a test sample, a method is used of measuring the mix rate of the modified crop based on the ratio of recombinant DNA to endogenous DNA that is always present in that crop.

In the case of corn for example, primer pairs have been developed that recognize each of the 5 lines of approved GMOs, along with a primer pair that recognizes the SSIIB gene region of endogenous corn DNA (JAS Analytical Handbook, Manual of Assessment and Analysis for Genetically Modified Foods, Revised Second Edition, IAA Center for Food Quality, Labeling and Consumer Services). Because this primer pair provides the standard for amount of endogenous DNA in recombinant DNA detection and quantification, the region of endogenous DNA to be amplified should be present in a single copy on the genome.

In "Concerning Testing Methods for Foods Modified by Recombinant DNA Technology (Partially Revised)" (Notice No. 1113001 of the Food Sanitation Department, Ministry of Health, Labor and Welfare, Nov. 13, 2003), the amplification products by specific primer pairs targeting endogenous corn or soy bean DNA and recombinant DNA are linked to a plasmid and used as the standard substance. The ratio of number of copies of recombinant DNA to number of copies of endogenous DNA can be accurately determined in a test sample by fixed-time quantitative PCR, by performing PCR using this standard substance.

When there are multiple GMO strains as in the case of corn, a particularly useful technique is to use a common standard substance to measure the contamination rate of each strain, which can be done by using a standard substance having endogenous DNA and DNA specific to each strain incorporated into a single circular DNA.

It is generally difficult to obtain genes specific to each strain, but once these have been incorporated into circular DNA, it is possible to provide a stable supply of strain-specific DNA by replicating the circular DNA itself.

SUMMARY

While no genetically modified products of common wheat (*Triticum aestivum*, hereunder sometimes called simply "wheat") have yet passed safety assessment, they are expected to appear on the market in the near future. Consequently, methods for detecting and quantifying endogenous wheat DNA and PCR primer pairs for use in such methods need to be developed in preparation for the distribution of GMO wheat. In terms of its genome structure and the nucleotide sequence of its genes, however, wheat shares a high degree of homology with other cereals such as barley, rye and oats. In addition to common wheat (*Triticum aestivum*), moreover, there is also durum wheat (*Triticum durum*). Durum wheat shares a particularly high degree of homology with common wheat since it possesses the (AA, BB) parts of the common wheat genome (AA, BB, DD), so the likelihood of false detection is high. There is therefore a need for methods capable of specifically detecting the endogenous DNA of common wheat without falsely detecting DNA derived from durum wheat and other cereal crops, or in other words for methods which avoid cross-reaction with other crops.

When there are multiple copies of an endogenous DNA region amplified by PCR, the wheat in the test sample cannot be assayed accurately, so in order to accurately assay the contamination rate of GMO wheat in a test sample it is desirable that the region of endogenous DNA to be amplified be present in only a single copy on the genome.

Moreover, when assessing GMO contamination by quantitative PCR, it is also useful in the case of wheat to use a standard substance comprising a region capable of being amplified by specific primer pairs targeting endogenous gene DNA and recombinant DNA linked on circular DNA.

It is therefore an object of the present invention to specify a partial sequence of wheat DNA (genome) that is present in a single copy and allows specific detection of wheat without cross-reactivity with other plants in PCR, and to provide primers for amplifying this partial sequence and a method for favorably detecting and assaying endogenous DNA using these primers.

It is another object of the present invention to provide a standard substance comprising a region capable of being amplified by specific primer pairs targeting endogenous gene DNA and recombinant DNA linked on circular DNA.

The inventors in this case perfected the present invention as a result of exhaustive research aimed at solving the aforementioned problems when they found that the WaxyD gene non-transcribed region, a region of the TaSUT1D gene coding for a sucrose transporter, a region of the CbpIII gene coding for carboxypeptidase III, the GSS (Genome Survey Sequence) sequence and the Lr1 gene (Leaf rust resistance gene) region are present in single copies in wheat genome DNA and do not have cross-reactivity with other plants in PCR, and discovered partial sequences which, when amplified, allow endogenous wheat DNA sequences to be specifically detected and assayed.

That is, the present invention relates to:

[1] A method for detecting or assaying endogenous wheat DNA in a test sample by PCR, comprising a step of using a nucleic acid in the sample or a nucleic acid extracted from the sample as the template to amplify the nucleic acid of a region comprising at least 80% or more of a nucleotide sequence represented by one of SEQ ID NOS:1-7 using a primer pair capable of amplifying that region, and a step of detecting or assaying the amplified nucleic acid;

[2] The method according to [1] above, wherein the primer pair is selected from the group consisting of (i) a primer pair consisting of a nucleic acid comprising the nucleotide sequence represented by SEQ ID NO:8 and a nucleic acid comprising the nucleotide sequence represented by SEQ ID NO:9, (ii) a primer pair consisting of a nucleic acid comprising the nucleotide sequence represented by SEQ ID NO:10 and a nucleic acid comprising the nucleotide sequence represented by SEQ ID NO:11, (iii) a primer pair consisting of a nucleic acid comprising the nucleotide sequence represented by SEQ ID NO:12 and a nucleic acid comprising the nucleotide sequence represented by SEQ ID NO:13, (iv) a primer pair consisting of a nucleic acid comprising the nucleotide sequence represented by SEQ ID NO:14 or 16 and a nucleic acid comprising the nucleotide sequence represented by SEQ ID NO:15 or 17, (v) a primer pair consisting of a nucleic acid comprising the nucleotide sequence represented by SEQ ID NO:18 and a nucleic acid comprising the nucleotide sequence represented by SEQ ID NO:19, (vi) a primer pair consisting of a nucleic acid comprising the nucleotide sequence represented by SEQ ID NO:20 and a nucleic acid comprising the nucleotide sequence represented by SEQ ID NO:21, and (vii) primer pairs consisting of pairs of nucleic acids with each nucleic acid comprising the continuous sequence of at least 80% of the nucleotide sequence of a nucleic acid in one of the primer pairs (i) to (vi);

[3] A method according to [1] or [2] above wherein the primers in the primer pair are nucleic acids 15 to 40 nucleotides in length;

[4] A primer pair for detecting or assaying wheat in a test sample by PCR, wherein said primer pair is capable of amplifying a region comprising at least 80% of a nucleotide sequence represented by any one of SEQ ID NOS:1 through 7.

[5] The primer pair according to [4] above, selected from the group consisting of (i) a primer pair consisting of a nucleic acid comprising the nucleotide sequence represented by SEQ ID NO:8 and a nucleic acid comprising the nucleotide sequence represented by SEQ ID NO:9, (ii) a primer pair consisting of a nucleic acid comprising the nucleotide sequence represented by SEQ ID NO:10 and a nucleic acid comprising the nucleotide sequence represented by SEQ ID NO:11, (iii) a primer pair consisting of a nucleic acid comprising the nucleotide sequence represented by SEQ ID NO:12 and a nucleic acid comprising the nucleotide sequence represented by SEQ ID NO:13, (iv) a primer pair consisting of a nucleic acid comprising the nucleotide sequence represented by SEQ ID NO:14 or 16 and a nucleic acid comprising the nucleotide sequence represented by SEQ ID NO:15 or 17, (v) a primer pair consisting of a nucleic acid comprising the nucleotide sequence represented by SEQ ID NO:18 and a nucleic acid comprising the nucleotide sequence represented by SEQ ID NO:19, (vi) a primer pair consisting of a nucleic acid comprising the nucleotide sequence represented by SEQ ID NO:20 and a nucleic acid comprising the nucleotide sequence represented by SEQ ID NO:21, and (vii) primer pairs consisting of pairs of nucleic acids with each nucleic acid comprising the continuous sequence of at least 80% of the nucleotide sequence of a nucleic acid in one of the primer pairs (i) to (vi);

[6] A kit for detecting or assaying an endogenous wheat DNA sequence in a test sample by PCR, comprising a primer pair according to [4] or [5] above;

[7] Circular DNA comprising endogenous DNA common to both genetically modified wheat and non-genetically modified wheat along with one or more pieces of genetically modified wheat-specific DNA each comprising a sequence specific to a strain of genetically modified wheat;

[8] Circular DNA comprising DNA comprising a nucleotide sequence having at least 80% homology with a nucleotide sequence represented by any one of SEQ ID NOS:1 through 7;

[9] Circular DNA comprising a region capable of being amplified by PCR using a primer pair according to [4] or [5] above;

[10] Circular DNA according to [9] or [10] above, further comprising 1 or more pieces of DNA each comprising a sequence particular to a specific strain of genetically modified wheat;

[11] A method for determining the contamination rate of genetically modified wheat in a test sample, comprising: performing quantitative PCR using, as templates, the circular DNA described in any one of [7] through [10] above and DNA extracted from the test sample; using the results of the quantitative PCR for the circular DNA to prepare a calibration curve for determining the number of molecules of template DNA; using the calibration curve and the results of the quantitative PCR for the test sample to determine the number of molecules of a partial sequence of an endogenous wheat DNA sequence and the number of molecules of a partial sequence of a DNA sequence specific to at least one kind of genetically modified wheat contained in the test sample; and determining the ratio A obtained by dividing the number of molecules of the partial sequence of the DNA sequence specific to the genetically modified wheat by the number of molecules of the partial sequence of the endogenous wheat DNA sequence;

[12] The method according to [11] above, further comprising a step of determining the contamination rate of genetically modified wheat in a sample by calculating the formula 100× NB using the ratio A and the ratio B obtained by dividing the number of molecules, obtained by quantitative PCR using as the template DNA extracted from standard seeds of genetically modified wheat, of a partial sequence of a DNA sequence specific to a particular strain of genetically modified wheat by the number of molecules of a partial sequence of an endogenous wheat DNA sequence;

[13] A method according to [11] or [12] above, wherein at least one primer pair selected from the primer pairs described in [4] and [5] is used in said quantitative PCR.

The method of the present invention provides accurate information about the presence and amount of wheat in test samples of food materials and processed foods, etc., and therefore the PCR primer pairs used in the present invention need to specifically detect wheat without any cross-reactions by crops other than wheat such as rice, barley, rye, oats, "minorimugi" barley, corn, soy beans, potatoes, tomatoes, eggplants, foxtail millet, Chinese millet, buckwheat, rapeseed, etc. Moreover, the endogenous DNA region to be amplified by the primer pair of the present invention is preferably a single copy.

If the PCR primer pair is cross-reactive with a crop other than wheat in an assessment method, not only may there be false-positive results for wheat detection but it will be difficult to accurately quantify the endogenous wheat DNA in the test sample. Similarly, endogenous wheat DNA cannot be accurately assayed if the endogenous DNA region is present in multiple copies. Consequently, such methods and primer pairs cannot accurately determine the contamination rate of GMO wheat.

The present invention provides a method capable of specifically detecting or quantifying endogenous wheat DNA in test samples of food materials, processed foods and the like without cross-reacting with other crops, along with PCR primer pairs for use in this method. This method detects or assays by PCR a specific partial sequence of an endogenous DNA sequence which has low homology with grains other than wheat and which is present in only a single copy on the genome.

Moreover, using the standard substance for detecting GMO wheat provided by the present invention it is possible to accurately determine the contamination rate of GMO wheat in a test sample for each GMO strain by quantitative PCR.

DETAILED DESCRIPTION

Figure 1:
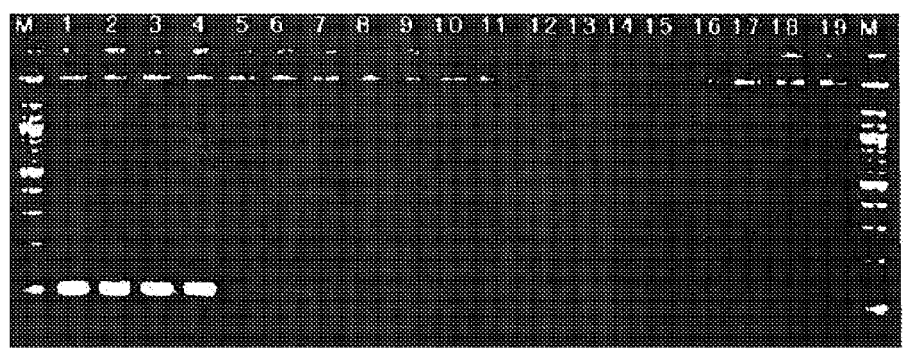
FIG. 1 shows results for wheat specificity test of the primer pair Wx011-5'/3'. Of the lanes, M shows the 100 bp ladder marker, 1 is wheat brand 1CW, 2 is wheat brand WW, 3 is wheat brand N61, 4 is wheat flower, 5 is rice, 6 is barley, 7 is corn, 8 is soy beans, 9 is potatoes, 10 is tomatoes, 11 is eggplant, 12 is rye, 13 is Minorimugi, 14 is oats, 15 is foxtail millet, 16 is Chinese millet, 17 is buckwheat, 18 is rapeseed and 19 is the No Template Control (water).

The terms used in these specifications are defined below, and the present invention is explained in detail.

In these specifications, the term "wheat" indicates common wheat (*Triticum aestivum*) unless otherwise specified.

The method of the present invention detects as an endogenous DNA sequence of wheat, specific parts of the regions of the WaxyD gene nontranscribed region and its 3' upstream region (SEQ ID NO:16), the TaSUT1D gene (Accession No. AF408845), the CbpIII gene (Accession No. J02817), the Lr1 gene (Accession No. 579983) and the GSS sequence (Accession No. AJ440705) on the wheat genome.

A total of three sets of the Waxy gene are known to exist, one each on the wheat 4A, 7A and 7D chromosomes (Japanese Patent Application Laid-open No. 2003-284598 and Ainsworth, C. et al., Plant Mol. Biol. 1993 April, 22(1):67-82). It is difficult to detect the full length WaxyD gene from the wheat genome in a processed food, while the region of a partial sequence selected at random may be multiple-copy sequence.

The present inventors determined the nucleotide sequence (SEQ ID NO:22) of the nontranscribed region of the WaxyD gene, discovered the existence in that region of a single copy region present only in genome D, and named a 101 bp part of this the Wx011 region (SEQ ID NO:2). A 102 bp part was named the Wx012 region (SEQ ID NO:1). In the method of the present invention, the WaxyD gene is detected and quantified by amplifying a region comprising at least 80% of the Wx011 region or Wx012 region by PCR.

The TaSUT gene is known as a sucrose transporter gene, and the wheat A, B and D chromosomes have been reported to each contain 1 copy of the TaSUT gene with highly homologous nucleotide sequences (Aoki, N. et al., Plant Molecular Biology 50:453-462, 2002). However, in the present invention it was discovered that, of the regions of the genome D TaSUT1D gene, the sut01 region (SEQ ID NO:3) and sut02 region (SEQ ID NO:4) might be present only in single copies on the D chromosome. Therefore, the present invention also relates to a method for detecting and quantifying the TaSUT1D gene by amplifying a region comprising at least 80% of the sut01 region (SEQ ID NO:3) and/or sut02 region (SEQ ID NO:4) by PCR.

Of the regions of the CbpIII gene on the genome the 100 bp CbpIII014 region (SEQ ID NO:5) is probably a single copy, and was confirmed to have almost no cross-reactivity with other plant varieties in qualitative PCR. The present invention therefore relates to a method for detecting and quantifying the CbpIII gene by amplifying a region comprising at least 80% of the CbpIII014 region (SEQ ID NO:5) by PCR.

The wheat GSS region is DNA that has a promoter-like function in genome analysis. Of the GSS region, the 111 bp gss01 region (SEQ ID NO:6) is probably a single copy, and was confirmed to have almost no cross-reactivity with other plant varieties in qualitative PCR. The present invention therefore relates to a method for detecting and assaying the gss01 region by amplifying a region comprising at least 80% of the gss01 (SEQ ID NO:6) region by PCR.

Of the regions of the Lr1 gene in the wheat genome, the 111 bp Lr101 region (SEQ ID NO:7) is probably a single copy, and was confirmed to have almost no cross-reactivity with other plant varieties in qualitative PCR. The present invention therefore relates to a method for detecting and assaying the Lr1 gene by amplifying a region comprising at least 80% of the Lr101 region (SEQ ID NO:7) by PCR.

Because the aforementioned Wx011 region, Wx012 region, sut01 region, sut02 region, CbpIII014 region, gss01 region and Lr101 region are all short (roughly 100-130 bp), they allow endogenous wheat DNA to be detected and quantified even in processed foods and other samples in which the DNA may have become fragmented.

In the specifications of this application, a "region comprising at least 80% of a nucleotide sequence represented by any one of SEQ ID NOS:1 through 7" is either a shorter region comprising the continuous sequence of at least 80% of the nucleotide sequence represented by any one of SEQ ID NOS:1 through 7, or a longer region comprising the nucleotide sequence represented by any one of SEQ ID NOS:1 through 7 along with the 5' end and/or 3' end nucleotide sequence on the genome, wherein at least 80% of the whole constitutes the nucleotide sequence represented by any one of SEQ ID NOS:1 through 7. Because this region encompasses at least 80% of a single copy region, a PCR product of the expected length can be obtained by selecting appropriate primer pairs even if the region is shorter or longer than the nucleotide sequence represented by SEQ ID NOS:1 through 7, allowing endogenous wheat DNA to be detected and/or assayed.

The primer pair used in PCR in the present invention is not particularly limited as long as it is capable of amplifying a region of at least 80% of the Wx011 region, Wx012 region, sut01 or sut02 region, CbpIII014 region, gss01 region or Lr101 region, and can be designed based on the nucleotide sequence of the region to be amplified in accordance with the basic rules of primer preparation. In this case, care should be taken as to the uniformity of the Tm values of the primers. Each primer should be normally 15 to 40 bp or preferably 15 to 30 bp long.

If the PCR primer pair cross-reacts with a crop other than wheat, not only may there be false-positive results for wheat detection, but it will be difficult to accurately quantify the endogenous wheat DNA sequence in the sample. It will also be impossible to accurate assay an endogenous wheat DNA sequence if there are multiple copies of the endogenous DNA sequence. Therefore, such methods and primer pairs cannot accurately determine the mix rate of GMO wheat.

The method of the present invention provides accurate information about the presence and amount of wheat in test samples of food materials, processed foods, and the like, and therefore the PCR primer pairs used in the present invention need to specifically detect wheat without any cross-reactions with crops other than wheat such as rice, durum, barley, rye, oats, "minorimugi" barley, corn, soy beans, potatoes, tomatoes, eggplants, foxtail millet, Chinese millet, buckwheat, rapeseed, etc.

Examples of such primer pairs include (i) a primer pair consisting of a nucleic acid comprising the nucleotide sequence represented by SEQ ID NO:8 and a nucleic acid comprising the nucleotide sequence represented by SEQ ID NO:9, (ii) a primer pair consisting of a nucleic acid comprising the nucleotide sequence represented by SEQ ID NO:10 and a nucleic acid comprising the nucleotide sequence represented by SEQ ID NO:11, (iii) a primer pair consisting of a nucleic acid comprising the nucleotide sequence represented by SEQ ID NO:12 and a nucleic acid comprising the nucleotide sequence represented by SEQ ID NO:13, (iv) a primer pair consisting of a nucleic acid comprising the nucleotide sequence represented by SEQ ID NO:14 or 16 and a nucleic acid comprising the nucleotide sequence represented by SEQ ID NO:15 or 17, (v) a primer pair consisting of a nucleic acid comprising the nucleotide sequence represented by SEQ ID NO:18 and a nucleic acid comprising the nucleotide sequence represented by SEQ ID NO:19, (vi) a primer pair consisting of a nucleic acid comprising the nucleotide sequence represented by SEQ ID NO:20 and a nucleic acid comprising the nucleotide sequence represented by SEQ ID NO:21, and (vii) primer pairs consisting of pairs of nucleic acids with each nucleic acid comprising the continuous sequence of at least 80% of the nucleotide sequence of a nucleic acid in one of the primer pairs (i) to (vi) above. These primer pairs specifically amplify the Wx011 region, Wx012 region, sut01 or sut02 region, CbpIII014 region, gss01 region or Lr101 region without crossing with other crops.

The "primers consisting of nucleic acids each comprising the continuous sequence of at least 80% of the nucleotide sequence of each primer" are primers each comprising the continuous sequence of at least 80% of one of the nucleotide sequences represented by SEQ ID NO:8 through 21, which may be shifted towards the 5' end or 3' end of the genome nucleotide sequence and may be shorter, longer or identical. Consequently, among the primer pairs (vii) above, either the forward primer, the reverse primer or both of them consisting of nucleotide sequences represented by SEQ ID NOS:8 through 21 may be modified according to the aforementioned conditions. However, because these primers comprise at least 80% of nucleotide sequences represented by SEQ ID NOS:8 through 21, like the primer pairs (i) through (vi) above, they can specifically amplify the Wx011 region, Wx012 region, sut01 or sut02 region, CbpIII014 region, gss01 region or Lr101 region without cross-reacting with other crops.

The test samples used in the present invention are food materials or processed foods that contain or may contain wheat, including for example raw wheat seeds, dried seeds, wheat flour, mixed flour and other raw foodstuffs and intermediate processed foodstuffs, as well as processed foods such as bread and noodles. These food materials and products are not limited to human foods but also include pet foods and feed. Crops other than wheat include all crops used as food materials and raw foodstuffs, such as those mentioned above.

Nucleic acids can be extracted from this sample either as is or after it has been pulverized, or else after it has been washed, dried and pulverized. The nucleic acids extracted from the test sample and used in analysis are normally DNA. The DNA may be extracted by any known method, and may be extracted using one of the many DNA extraction kits currently on the market. For example, DNA can be extracted from the test sample using a DNeasy Plant Maxi Kit (QIAGEN) in accordance with the methods described in the JAS Analytical Handbook, Manual of Assessment and Analysis for Genetically Modified Foods, Revised Second Edition (IAA Center for Food Quality, Labeling and Consumer Services). The concentration of the extracted DNA is measured by absorption, and it is preferably used after having been diluted to a suitable concentration for PCR.

In the method of the present invention, PCR can be performed in accordance with ordinary methods taking into consideration the primers and DNA polymerase used. The PCR buffer, dNTP, $MgCl_2$ and other reagents may be prepared, or a commercial PCR kit may be used. One or two or more pairs of the aforementioned primers may be used in PCR. The PCR conditions may be for example 40 cycles of a cycle of 30 seconds at 95° C., 30 seconds at 63° C. and 30 seconds at 72° C., followed by 7 minutes at 72° C. for the final reaction, but these conditions can be changed as appropriate taking into consideration the Tm of the primers used, the length of the region to be amplified, the concentration of template DNA and the like.

The amplified nucleic acid (PCR product) can be detected using any method capable of identifying a specific DNA fragment, such as agarose gel electrophoresis, acrylamide gel electrophoresis, capillary electrophoresis, hybridization, immunological methods or the like. In general, the PCR product is electrophoresed and identified based on the electrophoresis pattern, but detection can also be accomplished by identifying a band produced by electrophoresis using 0.8% agarose gel containing ethidium bromide.

The present invention encompasses the primer pairs used in the aforementioned detection or assay method and a kit containing these primer pairs. The primers can be manufactured by ordinary methods. In addition to the primer pairs, the kit may include other reagents such as dNTP, $MgCl_2$, Taq DNA polymerase and other polymerases, buffer (such as Tris-HCl), glycerol, DMSO, positive control DNA, negative control DNA, distilled water and the like. These reagents may be packaged individually within the kit, or two or more reagents can be provided mixed with one another. The concentrations of the various reagents in the kit are not particularly limited as long as they are such as to allow the PCR of the present invention. The kit may consist only of the primer reagents or may also include desirable PCR conditions and other information.

The present invention also provides a standard substance useful for measuring the contamination rate of GMO wheat by quantitative PCR. This standard substance comprises endogenous DNA common to both non-GMO wheat and GMO wheat along with one or more pieces of GMO wheat-specific DNA linked on a single circular DNA.

The standard substance of the present invention may be circular DNA comprising, as the endogenous DNA, DNA consisting of a nucleotide sequence having at least 80% homology with any one of the nucleotide sequences represented by SEQ ID NOS1 through 7.

It may also be circular DNA comprising, as the endogenous DNA, a region capable of being amplified by a primer pair selected from the group consisting of (i) a primer pair consisting of a nucleic acid comprising the nucleotide sequence represented by SEQ ID NO:8 and a nucleic acid comprising the nucleotide sequence represented by SEQ ID NO:9, (ii) a primer pair consisting of a nucleic acid comprising the nucleotide sequence represented by SEQ ID NO:10 and a nucleic acid comprising the nucleotide sequence represented by SEQ ID NO:11, (iii) a primer pair consisting of a nucleic acid comprising the nucleotide sequence represented by SEQ ID NO:12 and a nucleic acid comprising the nucleotide sequence represented by SEQ ID NO:13, (iv) a primer pair consisting of a nucleic acid comprising the nucleotide sequence represented by SEQ ID NO:14 or 16 and a nucleic acid comprising the nucleotide sequence represented by SEQ ID NO:15 or 17, (v) a primer pair consisting of a nucleic acid comprising the nucleotide sequence represented by SEQ ID NO:18 and a nucleic acid comprising the nucleotide sequence represented by SEQ ID NO:19, (vi) a primer pair consisting of a nucleic acid comprising the nucleotide sequence represented by SEQ ID NO:20 and a nucleic acid comprising the nucleotide sequence represented by SEQ ID NO:21, and (vii) primer pairs consisting of pairs of nucleic acids with each nucleic acid comprising the continuous sequence of at least 80% of the nucleotide sequence of a nucleic acid in one of the primer pairs (i) to (vi) above.

The circular DNA used for the standard substance is not particularly limited as long as it allows insertion of endogenous DNA and GMO wheat strain-specific DNA, but for example a pBR vector (pBR322, pBR328, etc.), pUC vector (pUC19, pUC18, etc.) or λ-phage vector (λgt10, λgt11, etc.) or a commercial vector comprising one of these with modifications or the like can be used.

When detecting GMO wheat, it is necessary not only to amplify and detect an exogenous DNA sequence inserted into the normal wheat genome by genetic recombination, but to amplify a region including the endogenous sequences upstream and downstream from the exogenous DNA sequence. Because the identical exogenous DNA sequence may be inserted into other crops to prepare GMO crops, if only the exogenous DNA sequence is detected it will not be clear whether it is derived from GMO wheat or from another genetically modified crop. Consequently, primers for detecting GMO strain-specific sequences need to be primers capable of amplifying regions comprising the endogenous sequences upstream and downstream from the exogenous DNA sequences inserted into each strain of GMO wheat. These primers are prepared according to the methods described with respect to soy beans for example (Wurz, A. et al., $2^{nd}$ Status report: BgVV, BgVV-Heft, 1/199797, 118 or Kopell, E. et al., Mitt. Gebiete Levensm, Hyg., 88, 164, etc.), or analogous methods. A DNA sequence capable of being amplified by these primers is selected as the GMO wheat strain-specific sequence to be inserted into the standard substance.

Once the endogenous wheat DNA and GMO wheat-specific DNA to be inserted into the standard substance have been determined, PCR is performed using a normal wheat genome or GMO wheat genome as the template to clone the endogenous DNA and GMO wheat-specific DNA, and the cloned DNA fragments and the cloning site of the aforementioned circular DNA are cleaved with the same restriction enzyme to link the DNA fragments to the cleaved site of the circular DNA. A known restriction enzyme can be selected as appropriate, and for example EcoRI, SpeI, EcoRV, SmaI, SacI, NotI, HindIII, XhoI or the like can be used.

Calibration curves can be derived for the partial sequences of the endogenous wheat DNA sequence and GMO-specific DNA sequence by preparing a dilution series of two or more concentrations of a solution comprising the resulting standard substance, and subjecting each to quantitative PCR. Moreover, the standard substance of the present invention can be used as a positive control for the endogenous wheat DNA sequence or GMO-specific DNA sequence in qualitative PCR.

The present invention encompasses a method for determining the contamination rate of GMO wheat in a test sample by PCR using the aforementioned standard substance.

In this method, quantitative PCR is performed using as templates the aforementioned standard substance and DNA extracted from the test sample, and a calibration curve for determining the number of molecules of template DNA is prepared using the results of quantitative PCR for the standard substance.

In quantitative PCR, the Ct value is used as data. The Ct value is the cycle number (threshold cycle) at which a specific amount of amplification product is reached as amplification becomes exponential when changes in the amount of amplified product are followed over time in quantitative PCR. The aforementioned calibration curve can be used to convert this Ct value into the initial number of molecules of DNA (number of molecules of template DNA) contained in the test sample before PCR.

The calibration curve can be prepared according to known methods or similar methods with for example the Ct value plotted on the vertical axis and the logarithm of the number of molecules of standard substance in the dilution series on the horizontal axis. For example, it can be prepared by preparing a dilution series containing various concentrations of the standard substance and deriving the Ct values for each following a fixed period of quantitative PCR.

The initial number of molecules of a partial sequence of the endogenous wheat DNA sequence contained in the test sample and the number of molecules of a partial sequence of a DNA sequence specific to genetically modified wheat can be derived using the aforementioned calibration curve from the Ct values or in other words from the results of quantitative PCR performed on the test sample.

The resulting number of molecules of the partial sequence of a DNA sequence specific to genetically modified wheat can be divided by the number of molecules of the partial sequence of an endogenous wheat DNA sequence to obtain ratio A, while the number of molecules of a partial sequence of a DNA sequence specific to each strain of GMO wheat obtain by quantitative PCR using standard seeds of genetically modified wheat can be divided by the number molecules of the partial sequence of an endogenous wheat DNA sequence to obtain ratio B, and the contamination rate of genetically modified wheat in the test sample can be determined by calculating the formula 100×A/B. This ratio B is called the "internal standard ratio" in the JAS Analytical Handbook, Manual of Assessment and Analysis for Genetically Modified Foods, Revised Second Edition, IAA Center for Food Quality, Labeling and Consumer Services, and is the (recombinant gene)/(endogenous gene) ratio in DNA extracted from seeds of each pure GM strain. The internal standard ratio is constant in each strain of recombinant seeds.

The PCR steps in the method of the present invention for determining the GMO wheat contamination rate can be performed either simultaneously or separately. When the PCR steps are performed separately, the conditions should be such as to produce roughly the same nucleic acid amplification efficiency as in the PCR for determining the calibration curve. An example of such conditions would be the same temperatures and cycles as in the PCR for preparing the calibration curve.

Example 1

WaxyD Gene Detection

Detection was accomplished by amplifying the 101 bp Wx011 region (SEQ ID NO:2) and 102 bp Wx 012 region (SEQ ID NO:1), which are nontranscribed regions of the WaxyD gene.

[1] Primer Design

The primers were designed using the primer design software Primer Express (Applied Biosystems). The primers were designed in strict accordance with the basic rules of primer preparation, so that in addition to obtaining a uniform Tm value for each primer, the amplification product of PCR would be about 100 to 150 bp in order to allow detection in processed foods with DNA fragmentation, and the nucleotide length of each primer would be 18 to 25 bp. The 5' primer Wx011-5' (SEQ ID NO:8) and 3' primer Wx011-3' (SEQ ID NO:9) and the 5' primer Wx012-5' (SEQ ID NO:10) and 3' primer Wx012-3' (SEQ ID NO:11) were obtained as a result.

[2] DNA Extraction

For the PCR template DNA samples, DNA extracted from 2 brands (1CW, WW) and 4 varieties (including N61) of wheat and commercial wheat flour (Nisshin Flour Milling Co., Ltd. "Kameriya") was used for the wheat samples, while DNA extracted from rice, corn, foxtail millet, Chinese millet, buckwheat, 2 varieties of barley, rye, oats, soy beans, rapeseed, tomatoes, eggplant, and 1 brand (CAD) and 4 varieties (hereunder called "durum varieties A-D) of durum wheat were used as the comparative samples.

The wheat and other plant samples were washed with 1% SDS (Wako Pure Chemical Ind.), rinsed with distilled water and thoroughly dried, and then finely pulverized using a multi-bead shocker (Yasui Machines). DNA was extracted from 1 g of each pulverized sample using a DNeasy Plant Maxi Kit (QIAGEN) in accordance with the DNA extraction protocols for corn described in the JAS Analytical Handbook, Manual of Assessment and Analysis for Genetically Modified Foods, Revised Second Edition, IAA Center for Food Quality, Labeling and Consumer Services. For the durum wheat, 4 kernels of each variety were selected randomly and DNA was extracted from each kernel using the aforementioned kit in accordance with the attached protocols. The concentration of the extracted DNA was measured from the absorption, and part of it was diluted 10 ng/µL with pure water and used as the template DNA sample liquid in the PCR reaction.

[3] PCR Reaction and Electrophoresis

The PCR reaction liquids were prepared as follows. That is, 2.5 µL of DNA sample liquid prepared to 10 ng/µL was added to a liquid comprising PCR buffer (PCR buffer II, Applied Biosystems), 200 µmol/L dNTP, 1.5 mmol/L $MgCl_2$, 0.5 µmol/L 5' and 3' primers and 0.625 units of Taq DNA polymerase (Ampli Taq Gold, Applied Biosystems), for a total volume of 25 µL.

Using a GeneAmp PCR System 9600 (Applied Biosystems) as the PCR amplifier, the reaction conditions were set as follows. The temperature was maintained at 95° C. for 10 minutes to initiate the reaction, and PCR amplification was performed in 40 cycles of a cycle consisting of 30 seconds at 95° C., 30 seconds at 63° C. and 30 seconds at 72° C. The reaction liquid was then maintained for 7 minutes at 72° C. for the final reaction, stored at 4° C., and used as the PCR amplification reaction liquid.

Figure 2:
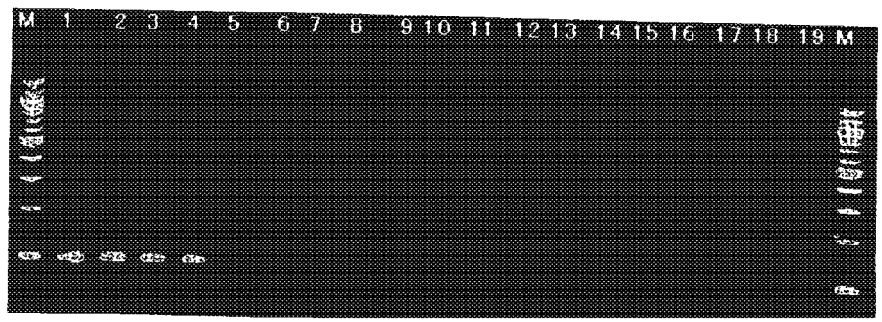
FIG. 2 shows results for wheat specificity test of the primer pair Wx012-5'/3'. Of the lanes, M is the 100 bp ladder marker, 1 is wheat brand 1 CW, 2 is wheat brand WW, 3 is wheat brand N61, 4 is wheat flower, 5 is rice, 6 is barley, 7 is corn, 8 is soy beans, 9 is potatoes, 10 is tomatoes, 11 is eggplant, 12 is rye, 13 is Minorimugi, 14 is oats, 15 is foxtail millet, 16 is Chinese millet, 17 is buckwheat, 18 is rapeseed and 19 is the No Template Control (water).

The PCR amplification reaction liquid was electrophoresed on 0.8% agarose gel containing ethidium bromide. The results of the detection tests for wheat and other crops are shown in FIG. 1 for Wx011-5Wx011-3' and in FIG. 2 for Wx012-5'/Wx012-3'.

Using either the primer pair Wx011-5'/Wx011-3' or the primer pair Wx012-5'/Wx012-3', a single band of the expected size was detected in the wheat sample (Lanes 1-4), but this band is not seen in the non-wheat lanes. This shows that the Wx011 region or Wx012 region of endogenous wheat DNA can be detected without crossing from other crops using the Wx011-5'/Wx011-3' or Wx012-5'/Wx012-3' primer pair.

The results for wheat and durum wheat using the Wx012-5'/Wx012-3' primer pair are shown in Table 1 below. These results confirm that wheat and durum wheat can be detected without crossing using the Wx012-5/Wx012-3' primer pair.

TABLE 1

| Lane No. | Template DNA | Detection primer wx012 5'/3' |
|---|---|---|
| 1 | Durum variety A | − |
| 2 | Durum variety B | − |
| 3 | Durum variety C | − |
| 4 | Durum variety D | − |
| 5 | Durum (CAD) | − |
| N | No template control (water) | − |
| P | Positive control (wheat) | + |

+: Amplification band of optimum size detected
−: Amplification band not detected Example 2

Confirmation of Number of Copies of Wx012 Region

Southern hybridization was performed under the following conditions to confirm the number of copies of Wx012.

DNA extracted from 2 varieties of wheat was used as the samples. DNA was extracted as in Example 1.

A Gene Images Alkphos Direct Labeling and Detection System (Amersham Biosciences) was used for hybridization and detection. The reagents, buffers and the like described in the kit protocols were used.

[1] Probe Design

Figure 3:
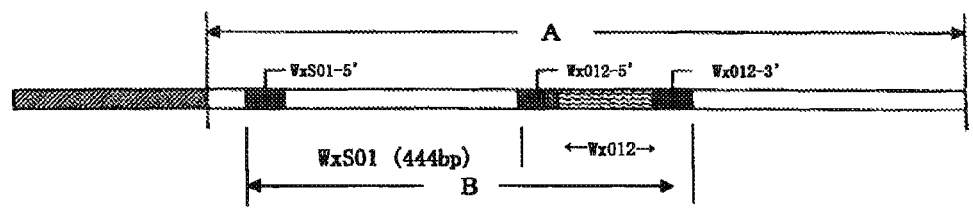
FIG. 3 shows the designing of the WxS01 probe for Southern hybridization to estimate the number of copies of Wx012. A shows the nontranscribed region and B shows the probe.

The length of a probe for obtaining good sensitivity in Southern hybridization using this kit is 300 bp or more. However, Wx012 is 102 bp in length, too short for Southern hybridization. Moreover the wheat genome is large, $1.7 \times 10^{10}$ bp, so in order to adequately enhance detection sensitivity a 444 bp WxS01 probe comprising the Wx012 region was designed and prepared by PCR using the 5' primer WxS01-5' (SEQ ID NO:23) and 3' primer Wx012-3' (SEQ ID NO:11). The primers for obtaining WxS01 were designed using Genetyx Win, in accordance with the basic rules of primer preparation so as to maintain a uniform Tm value for each primer. An outline of the primer design is shown in FIG. 3.

[2] Selection of Restriction Enzymes

Figure 4:
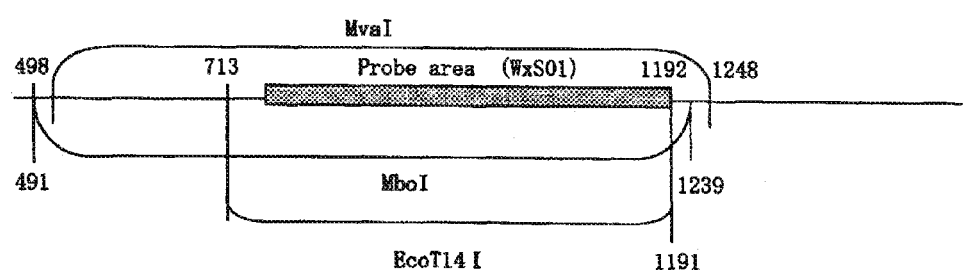
FIG. 4 shows the restriction enzyme cleavage sites of the WxS01 probe.

For the restriction enzymes, enzymes were selected on the condition that they did not cleave the target region and were not affected by methylation, and that the location of a cleavage site comprising the target was known. As a result, Mbol, Mval and EcoT14I were selected as being capable of cleaving both sides of the target region in a single enzyme reaction. The respective cleavage sites and fragment sizes are shown in FIG. 4. The restriction enzyme sites shown in FIG. 3 are locations on the nucleotide sequence represented by SEQ ID NO:22.

[3] Southern Hybridization of Wheat

The DNA was reacted for 15 hours at 37° C. with the aforementioned restriction enzymes. Following this reaction the product was subjected to phenol-chloroform treatment and ethanol sedimentation, and then dissolved in TE solution. The resulting DNA solution was electrophoresed with 1.6% agarose gel (LO3, TaKaRa Bio) using a TAE solution as the electrophoresis solution. Next, the DNA in the gel was transcribed overnight to a membrane (HyperBondN+, Amersham Pharmacia) using a 20×SSC solution.

Hybridization was performed at 55° C. using the hybridization buffer included in the kit. The WxS01 probe was adjusted to a concentration of 20 ng/ml and reacted overnight. This was washed for 20 minutes at 55° C. using the primary washing liquid and for 10 minutes at room temperature using the secondary washing liquid. After being washed, it was left for 3 minutes on the membrane on which the detection enzyme reaction had been initiated, and then wrapped in saran wrap after careful removal of the detection liquid. This was developed for 1 hour in a dark room with photosensitive film (Hyper film, Amersham Pharmacia), and the bands were evaluated.

Figure 5:
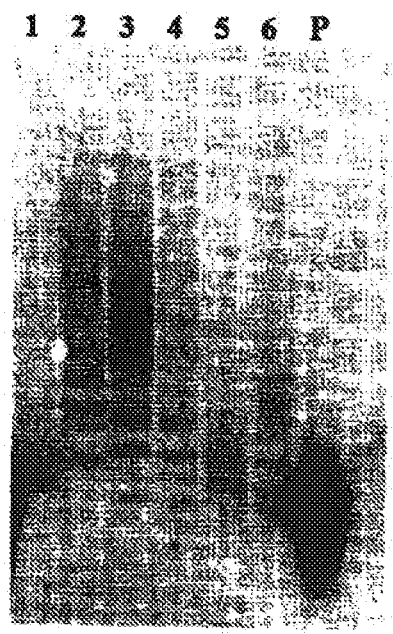
FIG. 5 shows the results of Southern hybridization for wheat using the WxS01 probe. Of the lanes, 1 shows the results for WW variety ΔΔ cleaved with Mbol, 2 for \NW variety ΔΔ cleaved with Mval, 3 for WW variety □□ cleaved with EcoT14I, 4 for HRS variety □□ cleaved with Mbol, 5 for HRS variety □□ cleaved with Mval, 6 for HRS variety □□ cleaved with EcoT14I, and P the results for cleavage with the Positive Control (Wxs01: 300 g).

As a result, 2 bands were detected after cleavage with Mbol, 3 after cleavage with Mval, and 3 or 6 after cleavage with EcoT14I (FIG. 5). Since it has been reported that there are 2 copies of the Waxy gene on genome A and 1 copy on genome D (Ainsworth, C. et al., Plant Mol. Biol. 1993 April, 22(1):67-82), this confirms that the region with which the WxS01 probe hybridizes is present in 2 copies on genome A and 1 copy on genome D.

[4] Southern Hybridization of Durum Wheat

Southern hybridization was performed as in [3] above using as the template durum wheat, which does not include a genome D.

Figure 6:
FIG. 6 shows the results of Southern hybridization for durum wheat. Of the lanes, 1 shows the results for durum variety ▼▼ cleaved with Mbol, 2 for durum variety ▼▼ cleaved with Mval, and 3 for durum variety ▼▼ cleaved with EcoT14I.

As a result, 1 band was detected after cleavage with Mbol, 2 after cleavage with Mval and 3 after cleavage with EcoT14I. However, of the 3 bands produced by EcoT14I one was thicker than the other two, representing a fusion of two bands, so it was determined that at most 4 bands were detected in durum wheat in this test (FIG. 6). These results match [3] above, which shows that 2 copies of WxS01 are present on genome A. It was also confirmed in Example 1 that the Wx012 region of endogenous DNA is present only on genome D. These results confirm that there is only one copy of the Wx012 region in the wheat genome.

Example 3

Confirming Suitability of Wx012 by Quantitative PCR

Next, it was confirmed that Wx012 meets the necessary conditions as an endogenous sequence for detection even in quantitative PCR.

[1] TaqMan Probe Design

This was designed using the primer and probe design software Primer Express (Applied Biosystems Japan). An appropriate probe was selected by checking the conditions for probe selection described in the software protocols. The nucleotide sequence of the designed probe is represented by SEQ ID NO:42.

[2] Test Samples

DNA extracted from 12 plants other than wheat (rice, corn, foxtail millet, Chinese millet, buckwheat, barley, rye, oats, soy beans, rapeseed, garbanzo beans, kidney beans), 4 typical varieties of durum wheat and 19 typical varieties of strong, medium-strength and low-strength wheat was used for the PCR template DNA samples.

[3] DNA Extraction

The wheat and other plant samples were each washed with 1% SDS (Wako Pure Chemical Ind.), rinsed with distilled water, thoroughly dried and fine pulverized using a multi-bead shocker (Yasui Machine). DNA was extracted from 1 g of each of the resulting powdered grain samples using a DNeasy Plant Maxi kit (Qiagen) in accordance with the corn DNA extraction protocols described in official methods. In the case of the durum wheat, 4 kernels of each variety were selected randomly, and DNA was extracted from each kernel in accordance with the protocols of the DNeasy Plant Mini Kit (Qiagen). In the case of 4 varieties of wheat, DNA was extracted using a Genomic-tip 20/G (Qiagen) and the CTAB method in accordance with the protocols described in official methods, and also with a DNeasy Plant Mini Kit (Qiagen) in accordance with the attached protocols. The concentration of the extracted DNA was measured by absorption, and part was diluted to 20 ng/μL with pure water and used as the template DNA sample liquid for the PCR reaction.

[4] Quantitative PCR Reaction

Quantitative PCR was performed using an ABI7700 (Applied Biosystems).

A 2-point or 3-point parallel analysis was performed on each sample. Each reaction was performed using a system of 25 μL per well.

The PCR reaction liquid was prepared as follows. Solutions of the Taq Man probe, 5' primer and 3' primer were diluted with pure water to 2 μM, 5 μM and 5 μM, and a solution of each of these and pure water mixed in proportions of 1:1:1:1 was used as the Primer-Probe Mix solution.

The necessary quantity of the master mix was prepared by mixing TaqMan Universal Master Mix (Applied Biosystems) and the Primer-Probe Mix solution at a ratio of 1.25:1. 72 μL of the master mix was dispensed for each template DNA, and 8 μL of each template DNA prepared to 20 ng/mL was added and thoroughly mixed. 25 μL of this mixture was dispensed to the designated wells on a 96-well plate, 3 wells per sample.

The reaction conditions were set as follows. The temperature was maintained at 50° C. for 2 minutes and then 95° C. for 10 minutes to initiate the reaction, followed by an amplification reaction of 40 cycles of a cycle of 30 seconds at 95° C. and 1 minute at 59° C., after which the temperature was maintained at 50° C. for 4 minutes.

[5] Confirming Wheat Specificity

Using DNA of 19 varieties of wheat and 12 other plants, DNA extracted from 4 varieties of durum wheat and DNA extracted from 12 plants other than wheat as templates, each sample was applied to 3 wells and quantitative PCR was performed.

As a result of quantitative PCR using the Wx012-5'/3' primers and TaqMan probe Wx012-T, no amplification curve was detected for NTC, but good amplification curves were obtained for the 19 varieties of wheat DNA. Amplification was not detected in the case of the DNA from 12 types of plants other than wheat or the DNA from 4 varieties of durum wheat.

[6] Confirming Linearity of Calibration Curve

Wheat DNA was prepared to 300 ng/μL, 150 ng/μL, 75 μL, 30 μL, 10 ng/μL, 4 ng/μL, 1 ng/μL and 0.1 ng/μL, and used as the standard template in quantitative PCR. A calibration curve was derived from the results according to the JAS Analytical Handbook, and the correlation coefficient was confirmed.

Figure 8:
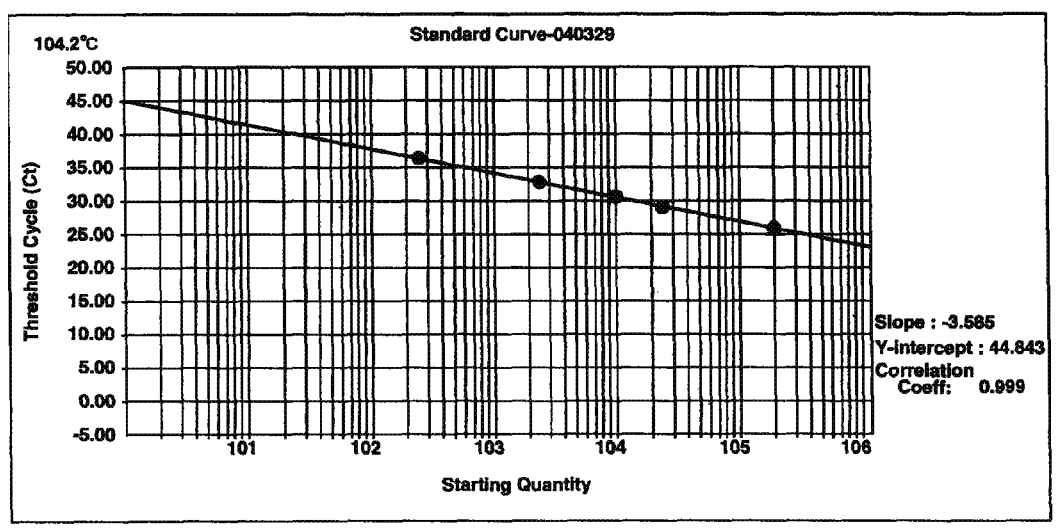
FIG. 8 is a calibration curve prepared from the results of quantitative PCR using as templates various concentrations of wheat DNA.

The resulting calibration curve is shown in FIG. 8. When wheat DNA prepared to 1-300 ng/μL or 0.1-75 μg/μL was applied as standard template DNA, a highly linear calibration curve was obtained, indicating that these can be used in quantitative testing.

Example 4

TaSUT1D Gene Detection

The sut01 region (SEQ ID NO:3) of the TaSUT1D gene and the sut02 region (SEQ ID NO:4) consisting of the described nucleotide sequence were amplified by PCR.

The primer pairs were designed as in the case of WaxyD above, and the 5' primer sut01-5' (SEQ ID NO:12) and 3' primer sut01-3' (SEQ ID NO:13) and the 5' primer sut02-5' (SEQ ID NO:14) and 3' primer sut02-3' (SEQ ID NO:15) were used in PCR testing. The results are shown in Table 2.

TABLE 2

| Template DNA | TaSUT detection primers | |
|---|---|---|
| | sut01-5'/3' | sut02-5'/3' |
| Wheat | + | + |
| Rice | − | − |
| Corn | − | − |
| Soy beans | − | − |
| Rye | − | − |
| Oats | − | − |
| Barley | − | − |
| Rapeseed | − | − |
| Foxtail millet | − | − |
| Chinese millet | − | − |
| Durum Brand E | − | − |
| NTC (water) | − | − |

+: Amplification band of optimum size detected
−: Amplification band not detected
NTC: No Template Control (water)

A single band (131 bp or 101 bp) of the anticipated size was detected using either primer pair in the case of wheat, while no band was detected in the case of other grains and durum wheat (genome configuration AaBb). When the same test was performed using multiple varieties of wheat, the anticipated single band was detected in each.

It has already been shown that the region from which these primer pairs were designed (Accession No. AF408845, 3924-4397; 474 bp) is present in one copy each in genomes A, B and D. The amplified regions sut01 and sut02 of sut01-573' and sut02-5'/3' are specific to wheat (genome configuration AaBbDd) in qualitative PCR and are not detected in durum wheat (genome configuration AaBb), confirming that the sut01 region and sut02 region are probably present in only one copy in genome D. This confirms that endogenous wheat DNA (TaSUT1D gene) can be detected using the primer pair sut01-5'/3' or sut02-5'/3' without crossing from other crops.

Example 5

Detection of CbpIII Gene

The CbpIII014 region (SEQ ID NO:5) of the CbpIII gene was amplified by PCR.

Figure 7:
FIG. 7 shows the results of a test confirming the wheat specificity of the primer pair Cbp014-5'/3'. Of the lanes, M shows the 100 bp ladder marker, 1 the wheat brand 1 CW, 2 the wheat brand WW, 3 the wheat brand N61, 4 wheat flour, 5 rice, 6 barley, 7 corn, 8 soy beans, 9 potatoes, 10 tomatoes, 11 eggplant, 12 rye, 13 Minorimugi, 14 oats, 15 foxtail millet, 16 Chinese millet, 17 buckwheat, 18 rapeseed, and 19 the No Template Control.

The primer pair was designed as in the case of WaxyD above, and PCR testing was performed using the 5' primer cbp014-6' (SEQ ID NO:16) and 3' primer cbp014-3' (SEQ ID NO:17). The results are shown in FIG. 7. A single band of the anticipated size (101 bp) was detected in the wheat lanes (Lanes 1-4), but no band was detected in the non-wheat lanes.

This confirms that endogenous wheat DNA (Cbp gene) can be detected using the primer pair cbp014-5'/cbp014-3' without crossing from other crops.

Example 6

Detection of GSS Sequence

The gss01 region (SEQ ID NO:6), gss02 region (SEQ ID NO:30) and gss03 region (SEQ ID NO:31) of the GSS sequence were amplified by PCR.

The primer pairs were designed as in the case of WaxyD, and PCR was performed using the gss01-5' (SEQ ID NO:18) and gss01-03' (SEQ ID NO:19) primers as the primer pair for the gss01 region, the gss02-5' (SEQ ID NO:34) and gss02-3' (SEQ ID NO:35) primers as the primer pair for the gss02 region, and the gss03-5' (SEQ ID NO:36) and gss03-3' (SEQ ID NO:37) primers as the primer pair for the gss03 region. The results are shown in Table 3.

[Table 3]

TABLE 3

Confirmation of specificity of GSS detection primers

| Template DNA | GSS detection primers | | |
|---|---|---|---|
| | gss01-5'/3' | gss02-5'/3' | gss03-5'/3' |
| Wheat | + | + | + |
| Durum wheat | − | Extra | + |
| Rice | − | − | − |
| Barley | − | − | − |
| Corn | − | + | − |
| Soy beans | − | − | − |
| Buckwheat | − | − | − |
| Oats | − | | |
| Rye | − | | |
| Chinese millet | − | | |
| Foxtail millet | − | | |
| Rapeseed | − | | |
| NTC | − | − | − |

+: Amplification band of optimum size detected
−: Amplification band not detected
Extra: Band of size different from optimum size detected
NTC: No Template Control (water)

In the case of wheat a single band of the anticipated size was detected using all three primer pairs. Some crossing by durum wheat and corn occurred with the gss02 and gss03 primer pairs, but no such crossing occurred with the gss01 primers, confirming that the gss01 primers are capable of detecting the endogenous wheat gene.

Example 7

The Lr101 region (SEQ ID NO:7), Lr102 region (SEQ ID NO:32) and Lr103 region (SEQ ID NO:33) of the Lr1 sequence were amplified by PCR.

The primer pairs were designed as in the case of WaxyD, and PCR was performed using the pair of primers represented by SEQ ID NO:20 and SEQ ID NO:21 for the Lr101 region, the pair of primers represented by SEQ ID NO:38 and SEQ ID NO:39 for the Lr102 region and the pair of primers represented by SEQ ID NO:40 and SEQ ID NO:41 for the Lr103 region. The results are shown in Table 4.

TABLE 4

Confirmation of specificity of Lr1 detection primers

| Template DNA | Lr1 detection primers | | |
|---|---|---|---|
| | Lr101-5'/3' | Lr102-5'/3' | Lr103-5'/3' |
| Wheat | + | + | + |
| Durum wheat | − | + | Extra |
| Rice | − | − | − |
| Barley | − | − | − |
| Corn | − | − | − |
| Soy beans | − | − | − |
| Buckwheat | − | − | − |
| Oats | − | | |
| Rye | − | | |
| Chinese millet | − | | |
| Foxtail millet | − | | |
| Rapeseed | − | | |
| NTC | − | − | − |

+: Amplification band of optimum size detected
−: No amplification band detected
Extra: Band of different size from optimum size detected
NTC: No Template Control (water)

In the case of wheat a single band of the anticipated size was detected using all three primer pairs. Some crossing by durum wheat occurred with the Lr102 and Lr103 primer pairs, but no such crossing occurred with the Lr101 primers, confirming that the Lr101 primers are capable of detecting the endogenous wheat gene.

COMPARATIVE EXAMPLE

Detection tests for endogenous wheat DNA were performed by PCR using (1) a 5' primer Cbp013-5' (SEQ ID NO:24)/3' primer Cbp013-3' (SEQ ID NO:25) primer pair designed based on the nucleotide sequence of the CbpIII gene, (2) a 5' primer TthV011-5' (SEQ ID NO:26)/3' primer TthV011-3' (SEQ ID NO:27) primer pair designed based on the nucleotide sequence of the TthV gene (Castagnaro A. et al., J. Mol. Biol. 1992 Apr. 20, 224(4):1003-9), and a 5' primer TthV012-5' (SEQ ID NO:28)/3' primer TthV012-3' (SEQ ID NO:29) primer pair designed based on the nucleotide sequence of the TthV gene similar to (3).

DNA extraction, PCR, electrophoresis and the like were performed as in the aforementioned examples.

Using primer pair (1), a single band of the anticipated size was detected from wheat, but the band was also confirmed from rice, barley, corn, rye, "minorimugi" barley, oats and foxtail millet, indicating crossing by multiple crops. Using primer pair (2), a single band of the anticipated size was detected from wheat, but there was crossing from barley. Using primer pair (3), a single band of the anticipated size was detected from wheat, but there was crossing from rye and "minorimugi" (a type of barley). The results are shown in Table 5 below.

TABLE 5

| | CbpIII primers | TthV primers | |
|---|---|---|---|
| Template DNA | Cbp013-5'/3' | TthV011-5'/3' | TthV012-5'/3' |
| Wheat | + | + | + |
| Rice | Extra | − | − |
| Barley | Extra | + | − |
| Corn | Extra | − | − |
| Soy beans | − | | |
| Potatoes | − | | |
| Tomatoes | − | − | − |
| Eggplant | − | − | − |

TABLE 5-continued

| | CbpIII primers | TthV primers | |
|---|---|---|---|
| Template DNA | Cbp013-5'/3' | TthV011-5'/3' | TthV012-5'/3' |
| Rye | Extra | | + |
| Barley ("Minorimugi") | Extra | | + |
| Oats | Extra | | − |
| Foxtail millet | Extra | | − |
| Chinese millet | − | | − |
| Buckwheat | − | | − |

TABLE 5-continued

| | CbpIII primers | TthV primers | |
|---|---|---|---|
| Template DNA | Cbp013-5'/3' | TthV011-5'/3' | TthV012-5'/3' |
| Rapeseed | − | | − |
| NTC | − | | − |

+: Amplification band of optimum size detected
−: No amplification band detected
NTC: No Template Control (water)
blank: not tested

We claim:

1. An isolated circular DNA comprising the nucleotide sequence of SEQ ID NO:4 capable of being amplified by PCR using a primer pair comprising a first primer comprising the nucleotide sequence of SEQ ID NO:14 and a second primer comprising the nucleotide sequence of SEQ ID NO:15.

2. The circular DNA according to claim 1, further comprising one or more pieces of DNA each comprising a sequence particular to a strain of genetically modified wheat.

3. A method for determining a mix rate of genetically modified wheat in a test sample, comprising:
   performing quantitative PCR using, as templates, DNA extracted from the test sample and a circular DNA comprising the nucleotide sequence of SEQ ID No:4 capable of being amplified by PCR using a primer pair comprising a first primer comprising the nucleotide sequence of SEQ ID NO:14 and a second primer comprising the nucleotide sequence of SEQ ID NO:15,
   preparing a calibration curve for determining the number of molecules of template DNA, using the results of the quantitative PCR for the circular DNA,
   determining the number of molecules having a partial sequence of an endogenous wheat DNA sequence and the number of molecules having a partial sequence of a DNA sequence present specifically in at least one kind of genetically modified wheat contained in the test sample, using the calibration curve and the results of the quantitative PCR for the test sample, and
   determining a ratio A obtained by dividing the number of molecules having a partial sequence of a DNA sequence present specifically in the genetically modified wheat by the number of molecules having a partial sequence of an endogenous wheat DNA sequence.

4. The method according to claim 3, further comprising:
   determining the mix rate of genetically modified wheat in a sample by calculating a formula 100×A/B using the ratio A and a ratio B obtained by dividing the number of molecules, obtained by quantitative PCR using as template DNA extracted from standard seeds of genetically modified wheat, having a partial sequence of a DNA sequence present specifically in a particular strain of genetically modified wheat by the number of molecules having a partial sequence of an endogenous wheat DNA sequence.

* * * * *

UNITED STATES PATENT AND TRADEMARK OFFICE
CERTIFICATE OF CORRECTION

| | | |
|---|---|---|
| PATENT NO. | : 8,722,397 B2 | Page 1 of 1 |
| APPLICATION NO. | : 13/218385 | |
| DATED | : May 13, 2014 | |
| INVENTOR(S) | : Hino et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Twenty-sixth Day of January, 2016

Michelle K. Lee
*Director of the United States Patent and Trademark Office*

SEQUENCE LISTING

```
<160> NUMBER OF SEQ ID NOS: 42

<210> SEQ ID NO 1
<211> LENGTH: 102
<212> TYPE: DNA
<213> ORGANISM: Triticum aestivum
<220> FEATURE:
<221> NAME/KEY: misc_feature
<223> OTHER INFORMATION: Wx012, WaxyD1 gene, non-transcribed region

<400> SEQUENCE: 1
ggtcgcagga acagaggtgt tcaaggcggc cgaaataggt tgccgcctgc ggcggaatcg      60
ccacccaccg tgaagttcac cgtttcgcaa tggaggaaca cc                        102

<210> SEQ ID NO 2
<211> LENGTH: 101
<212> TYPE: DNA
<213> ORGANISM: Triticum aestivum
<220> FEATURE:
<221> NAME/KEY: misc_feature
<223> OTHER INFORMATION: Wx011, WaxyD1 gene, non-transcribed region

<400> SEQUENCE: 2
agaaagaaaa ggaagttctg gtgcatggag cgtccatcca gtctgcaggg ttctcgtatg      60
gggagatagc cgcttgttgt agcgaagaag ggccgatata t                         101

<210> SEQ ID NO 3
<211> LENGTH: 131
<212> TYPE: DNA
<213> ORGANISM: Triticum aestivum
<220> FEATURE:
<221> NAME/KEY: misc_feature
<223> OTHER INFORMATION: sut01, TaSUT1D

<400> SEQUENCE: 3
gcccaaacca aaacgctatg actaatttca cttgattttg ccatggaatt tttagggtcc      60
agcgcgtgct ctgatggctg atttatcagg taacttttca tgacagttca gttatgctag     120
cgggttcagg c                                                          131

<210> SEQ ID NO 4
<211> LENGTH: 101
<212> TYPE: DNA
<213> ORGANISM: Triticum aestivum
<220> FEATURE:
<221> NAME/KEY: misc_feature
<223> OTHER INFORMATION: sut02, TaSUT1D gene

<400> SEQUENCE: 4
tcacttgatt ttgccatgga attttaggg tccagcgcgt gctctgatgg ctgatttatc       60
```

-continued

```
aggtaacttt tcatgacagt tcagttatgc tagcgggttc a                    101

<210> SEQ ID NO 5
<211> LENGTH: 100
<212> TYPE: DNA
<213> ORGANISM: Triticum aestivum
<220> FEATURE:
<221> NAME/KEY: misc_feature
<223> OTHER INFORMATION: CbpIII014, CbpIII gene

<400> SEQUENCE: 5
ccgcgatatg atcgataccg accaaagaag gggggaaaac tcgctaggtg gcccgttgcg    60
gtctcaagga gtgtctatct gtagctgtct gtttcctttc                         100

<210> SEQ ID NO 6
<211> LENGTH: 111
<212> TYPE: DNA
<213> ORGANISM: Triticum aestivum
<220> FEATURE:
<221> NAME/KEY: misc_feature
<223> OTHER INFORMATION: gss01, Genome Survey Sequence

<400> SEQUENCE: 6
gtgaagggca cacgatgtgc acgcgctgtt gagggcgccc gcagaatcgg cgatggctgc    60
tagttacagc ggaacacgcc aaacacagat gttggaaggc ccttcatcaa g            111

<210> SEQ ID NO 7
<211> LENGTH: 111
<212> TYPE: DNA
<213> ORGANISM: Triticum aestivum
<220> FEATURE:
<221> NAME/KEY: misc_feature
<223> OTHER INFORMATION: Lr101, Lr1 gene

<400> SEQUENCE: 7
cgcgggtgga gtccattatc caatgtcgtt tgggttcttt cccctgcaag tatctcggac    60
ttcaacttgc cattagacaa ctaacgaggg cggaatggca gcctatgttg g             111

<210> SEQ ID NO 8
<211> LENGTH: 24
<212> TYPE: DNA
<213> ORGANISM: Artificial Sequence
<220> FEATURE:
<223> OTHER INFORMATION: PCR probe Wx011-5'

<400> SEQUENCE: 8
agaaagaaaa ggaagttctg gtgc                                          24

<210> SEQ ID NO 9
<211> LENGTH: 24
<212> TYPE: DNA
<213> ORGANISM: Artificial Sequence
<220> FEATURE:
<223> OTHER INFORMATION: PCR primer Wx011-3'

<400> SEQUENCE: 9
atatatcggc ccttcttcgc taca                                          24

<210> SEQ ID NO 10
<211> LENGTH: 20
<212> TYPE: DNA
<213> ORGANISM: Artificial Sequence
<220> FEATURE:
<223> OTHER INFORMATION: PCR primer Wx012-5'

<400> SEQUENCE: 10
```

```
ggtcgcagga acagaggtgt                                          20

<210> SEQ ID NO 11
<211> LENGTH: 20
<212> TYPE: DNA
<213> ORGANISM: Artificial Sequence
<220> FEATURE:
<223> OTHER INFORMATION: PCR Primer Wx012-3'

<400> SEQUENCE: 11
ggtgttcctc cattgcgaaa                                          20

<210> SEQ ID NO 12
<211> LENGTH: 21
<212> TYPE: DNA
<213> ORGANISM: Artificial Sequence
<220> FEATURE:
<223> OTHER INFORMATION: PCR primer sut01-5'

<400> SEQUENCE: 12
gcccaaacca aaacgctatg a                                        21

<210> SEQ ID NO 13
<211> LENGTH: 20
<212> TYPE: DNA
<213> ORGANISM: Artificial Sequence
<220> FEATURE:
<223> OTHER INFORMATION: PCR primer sut01-3'

<400> SEQUENCE: 13
gcctgaaccc gctagcataa                                          20

<210> SEQ ID NO 14
<211> LENGTH: 22
<212> TYPE: DNA
<213> ORGANISM: Artificial Sequence
<220> FEATURE:
<223> OTHER INFORMATION: PCT primer sut02-5'

<400> SEQUENCE: 14
tcacttgatt ttgccatgga at                                       22

<210> SEQ ID NO 15
<211> LENGTH: 22
<212> TYPE: DNA
<213> ORGANISM: Artificial Sequence
<220> FEATURE:
<223> OTHER INFORMATION: PCT primer sut02-3'

<400> SEQUENCE: 15
tgaacccgct agcataactg aa                                       22

<210> SEQ ID NO 16
<211> LENGTH: 20
<212> TYPE: DNA
<213> ORGANISM: Artificial Sequence
<220> FEATURE:
<223> OTHER INFORMATION: PCR primer CbpIII014-5'

<400> SEQUENCE: 16
ccgcgatatg atcgataccg                                          20

<210> SEQ ID NO 17
<211> LENGTH: 25
<212> TYPE: DNA
<213> ORGANISM: Artificial Sequence
```

```
<220> FEATURE:
<223> OTHER INFORMATION: PCR primer CbpIII014-3'

<400> SEQUENCE: 17
ggaaaggaaa cagacagcta cagat                                          25

<210> SEQ ID NO 18
<211> LENGTH: 20
<212> TYPE: DNA
<213> ORGANISM: Artificial Sequence
<220> FEATURE:
<223> OTHER INFORMATION: PCR primer GSS01-5'

<400> SEQUENCE: 18
gtgaagggca cacgatgtgc                                                20

<210> SEQ ID NO 19
<211> LENGTH: 20
<212> TYPE: DNA
<213> ORGANISM: Artificial Sequence
<220> FEATURE:
<223> OTHER INFORMATION: PCR primer GSS01-3'

<400> SEQUENCE: 19
cttgatgaag ggccttccaa                                                20

<210> SEQ ID NO 20
<211> LENGTH: 20
<212> TYPE: DNA
<213> ORGANISM: Artificial Sequence
<220> FEATURE:
<223> OTHER INFORMATION: PCR primer Lr101-5'

<400> SEQUENCE: 20
cgcgggtgga gtccattatc                                                20

<210> SEQ ID NO 21
<211> LENGTH: 20
<212> TYPE: DNA
<213> ORGANISM: Artificial Sequence
<220> FEATURE:
<223> OTHER INFORMATION: PCR primer Lr101-3'

<400> SEQUENCE: 21
ccaacatagg ctgccattcc                                                20

<210> SEQ ID NO 22
<211> LENGTH: 1499
<212> TYPE: DNA
<213> ORGANISM: Triticum aestivum
<220> FEATURE:
<221> NAME/KEY: misc_feature
<223> OTHER INFORMATION: non-transcribed region, WaxyD1 gene

<400> SEQUENCE: 22
cgcgcccctg gctcaccagt atgatggccg gcgccgacgt gctcgccgtc accagccgct      60
tcgagccctg cggcctcatc cagctccagg ggatgcgcta cggaacggta aacttttcct    120
tcttgccaag tccttacttc ctgagcaatc atgagccatg cccatgaccg aagtttcttc    180
caaattttca gccgtgcgcg tgcgcgtcca ccggcgggct tgtcgacacg atcgtggagg    240
gcaagaccgg gttccacatg gccggctca gtgtcgatgt aagttcatca atctcttcaa     300
taaattcttc atcttgttca tcctgggagc tcaggcagat catcaaacgg gtttcctttt    360
tcctcttggt ggccagtgca acgtggtgga gccggccgac gtgaagaagg tggtgaccac    420
```

```
cctgaagcgc gccgtcaagg tcgtcggcac gccggcatac catgagatgg tcaagaactg    480
catgatacag gatctctcct ggaaggtaag tcagtctctg gtctggttta ggatgcattt    540
tccagaacaa ctaagagtta agactacaat ggtgctcttg ttcgatgtat ccattaatgg    600
tggcttgcgc atatggtgca ggggccagcc aagaactggg aggacgtgct tctggaactg    660
ggtgtcgagg ggagcgagcc gggggtcatc ggcgaggaga ttgcgccgct cgccatggag    720
aacgtcgccg ctccctgaag agagaaagaa aaggaagttc tggtgcatgg agcgtccatc    780
cagtctgcag ggttctcgta tggggagata ccgcttgtt gtagcgaaga agggccgata    840
tatataatat atagacttat aagtacttaa cttttgttgt gccgcttgcc tcttttacaa    900
acaaaaaaga agttaggggt tgtgcttgtt atagtgtgct gaactgtgct tgcattttgg    960
tgtggtatat tgcaataaac aaaggatttg ttatgtgttt ttgctattgg ttctccgtgt   1020
ttgagccgaa tcaagttatt ttgtgggggt ttcaaaggta cattttttgtg ttcttggagg   1080 tggcagcttc ggtcgcagga acagaggtgt tcaaggcggc cgaaataggt tgccgcctgc   1140
ggcggaatcg ccacccaccg tgaagttcac cgtttcgcaa tggaggaaca cctaggtgta   1200
agtttcaaaa tggcggcgcg atgaccgcca agatcaatgc gacacaacca ggaaatgaca   1260
gatgaccgcc aagatcaacg cacacaacaa atgacgcaag gggagcgatc atggctgaaa   1320
cagcttcact attttccttg ctagtacagt actacttgct cagtttgctg ttaaactgtg   1380
agtctgtgac gcgctaaact tatttaatga gttgtgcagc agcaacttat ttaatgtaag   1440
tcatgcaaag aggccagctt ctaaatactt cctaaaatac aaaaaaaaaa aaaaaaaa     1499
```

<210> SEQ ID NO 23
<211> LENGTH: 22
<212> TYPE: DNA
<213> ORGANISM: Artificial Sequence
<220> FEATURE:
<223> OTHER INFORMATION: PCR primer WxS01-5'

<400> SEQUENCE: 23
aaaaggaagt tctggtgcat gg                                              22

<210> SEQ ID NO 24
<211> LENGTH: 17
<212> TYPE: DNA
<213> ORGANISM: Artificial Sequence
<220> FEATURE:
<223> OTHER INFORMATION: CbpIII013-5'

<400> SEQUENCE: 24
ctggccacat ggtcccc                                                    17

<210> SEQ ID NO 25
<211> LENGTH: 17
<212> TYPE: DNA
<213> ORGANISM: Artificial Sequence
<220> FEATURE:
<223> OTHER INFORMATION: PCR primer CbpIII013-3'

<400> SEQUENCE: 25
acgtcgtcgc tggctcc                                                    17

<210> SEQ ID NO 26
<211> LENGTH: 20
<212> TYPE: DNA
<213> ORGANISM: Artificial Sequence
<220> FEATURE:
<223> OTHER INFORMATION: TthV011-5'
<220> FEATURE:

```
<221> NAME/KEY: misc_feature
<223> OTHER INFORMATION: TthV011-5'

<400> SEQUENCE: 26
agagtgcgat cgtgtgccta                                              20

<210> SEQ ID NO 27
<211> LENGTH: 26
<212> TYPE: DNA
<213> ORGANISM: Artificial Sequence
<220> FEATURE:
<223> OTHER INFORMATION: PCR primer TthV011-3'

<400> SEQUENCE: 27
tggagctatg cttcatgatt gcctaa                                       26

<210> SEQ ID NO 28
<211> LENGTH: 20
<212> TYPE: DNA
<213> ORGANISM: Artificial Sequence
<220> FEATURE:
<223> OTHER INFORMATION: PCR primer TthV012-5'

<400> SEQUENCE: 28
caggtgcaag tagagggcgt                                              20

<210> SEQ ID NO 29
<211> LENGTH: 21
<212> TYPE: DNA
<213> ORGANISM: Artificial Sequence
<220> FEATURE:
<223> OTHER INFORMATION: PCR primer TthV012-3'

<400> SEQUENCE: 29
tctgcgcact ggaacactgt a                                            21

<210> SEQ ID NO 30
<211> LENGTH: 111
<212> TYPE: DNA
<213> ORGANISM: Triticum aestivum
<220> FEATURE:
<221> NAME/KEY: misc_feature
<223> OTHER INFORMATION: gss02, Genome Survey Sequence

<400> SEQUENCE: 30
gctgcaatga gcatgtcgtg catgcgtgaa gggcacacga tgtgcacgcg ctgttgaggg    60
cgcccgcaga atcggcgatg gctgctagtt acagcggaac acgccaaaca c            111

<210> SEQ ID NO 31
<211> LENGTH: 111
<212> TYPE: DNA
<213> ORGANISM: Triticum aestivum
<220> FEATURE:
<221> NAME/KEY: misc_feature
<223> OTHER INFORMATION: gss03, Genome Survey Sequence

<400> SEQUENCE: 31
cggaacacgc caaacacaga tgttggaagg cccttcatca agctgtcagc aaactgggag    60
ttggtgggga tgtgttggac acggacttca ccaagagcag cgaactcccg a             111

<210> SEQ ID NO 32
<211> LENGTH: 111
<212> TYPE: DNA
<213> ORGANISM: Triticum aestivum
<220> FEATURE:
<221> NAME/KEY: misc_feature
```

<223> OTHER INFORMATION: Lr102, Lr1 gene

<400> SEQUENCE: 32
tggcagccta tgttggatca tgctaagaag tctgccccgg cctggcaaag aggcctcatc      60
catcgccctg gacggctcgt tttggtcaaa tcagtgattg cggctaaacc c              111

<210> SEQ ID NO 33
<211> LENGTH: 111
<212> TYPE: DNA
<213> ORGANISM: Triticum aestivum
<220> FEATURE:
<221> NAME/KEY: misc_feature
<223> OTHER INFORMATION: Lr103, Lr1 gene

<400> SEQUENCE: 33
gtctgggaat ccgcaacctt cagttgcaag gtttggcgtt gagagtgaga tgggaatgat      60
tgagacggac tgatccggag aggccatggc aaggcctccg atggcagtag a              111

<210> SEQ ID NO 34
<211> LENGTH: 20
<212> TYPE: DNA
<213> ORGANISM: Artificial Sequence
<220> FEATURE:
<223> OTHER INFORMATION: PCR primer gss02-5'

<400> SEQUENCE: 34
gctgcaatga gcatgtcgtg                                                  20

<210> SEQ ID NO 35
<211> LENGTH: 19
<212> TYPE: DNA
<213> ORGANISM: Artificial Sequence
<220> FEATURE:
<223> OTHER INFORMATION: PCR primer gss02-3'

<400> SEQUENCE: 35
gtgtttggcg tgttccgct                                                   19

<210> SEQ ID NO 36
<211> LENGTH: 20
<212> TYPE: DNA
<213> ORGANISM: Artificial Sequence
<220> FEATURE:
<223> OTHER INFORMATION: PCR primer gss03-5'

<400> SEQUENCE: 36
cggaacacgc caaacacaga                                                  20

<210> SEQ ID NO 37
<211> LENGTH: 20
<212> TYPE: DNA
<213> ORGANISM: Artificial Sequence
<220> FEATURE:
<223> OTHER INFORMATION: PCR primer gss03-3'

<400> SEQUENCE: 37
tcgggagttc gctgctcttg                                                  20

<210> SEQ ID NO 38
<211> LENGTH: 20
<212> TYPE: DNA
<213> ORGANISM: Artificial Sequence
<220> FEATURE:
<223> OTHER INFORMATION: PCR primer Lr102-5'

<400> SEQUENCE: 38

-continued

```
tggcagccta tgttggatca                                              20

<210> SEQ ID NO 39
<211> LENGTH: 20
<212> TYPE: DNA
<213> ORGANISM: Artificial Sequence
<220> FEATURE:
<223> OTHER INFORMATION: PCR primer Lr102-3'

<400> SEQUENCE: 39
gggtttagcc gcaatcactg                                              20

<210> SEQ ID NO 40
<211> LENGTH: 20
<212> TYPE: DNA
<213> ORGANISM: Artificial Sequence
<220> FEATURE:
<223> OTHER INFORMATION: PCR primer Lr103-5'

<400> SEQUENCE: 40
gtctgggaat ccgcaacctt                                              20

<210> SEQ ID NO 41
<211> LENGTH: 20
<212> TYPE: DNA
<213> ORGANISM: Artificial Sequence
<220> FEATURE:
<223> OTHER INFORMATION: PCR primer Lr103-3'

<400> SEQUENCE: 41
tctactgcca tcggaggcct                                              20

<210> SEQ ID NO 42
<211> LENGTH: 23
<212> TYPE: DNA
<213> ORGANISM: Artificial Sequence
<220> FEATURE:
<223> OTHER INFORMATION: PCR probe for detection of Wx012

<400> SEQUENCE: 42
caaggcggcc gaaataggtt gcc                                          23
```